(12) United States Patent
Guignard

(10) Patent No.: US 7,883,489 B2
(45) Date of Patent: Feb. 8, 2011

(54) DEVICE FOR IRRIGATING AND PRESSURIZING A CAVITY

(76) Inventor: Mireille Guignard, 145, chemin Vezely, Sergy (FR) F-01630

( * ) Notice: Subject to any disclaimer, the term of this patent is extended or adjusted under 35 U.S.C. 154(b) by 92 days.

(21) Appl. No.: 11/916,630

(22) PCT Filed: Jun. 9, 2005

(86) PCT No.: PCT/FR2005/001435

§ 371 (c)(1),
(2), (4) Date: Dec. 5, 2007

(87) PCT Pub. No.: WO2006/131609

PCT Pub. Date: Dec. 14, 2006

(65) Prior Publication Data

US 2008/0214994 A1    Sep. 4, 2008

(51) Int. Cl.
*A61M 1/00* (2006.01)
*A61M 31/00* (2006.01)
(52) U.S. Cl. .......................... 604/35; 604/65
(58) Field of Classification Search .............. 604/65
See application file for complete search history.

(56) References Cited

U.S. PATENT DOCUMENTS 4,696,669 A    9/1987   Menhusen et al.
4,902,276 A *  2/1990   Zakko ............................ 604/28
4,998,914 A *  3/1991   Wiest et al. .................... 604/67
5,195,960 A    3/1993   Hossain et al.

FOREIGN PATENT DOCUMENTS

FR          2766083 A       1/1999

OTHER PUBLICATIONS

International Search Report of PCT/FR2005/001435, date of mailing Feb. 21, 2006.
Notification of Transmittal of Translation of the International Preliminary Report on Patentability (Form PCT/IB/338) of International Application No. PCT/FR2005/001435 dated Feb. 14, 2008 with Forms PCT/ISA/373 and English translation form PCT/ISA/237.

* cited by examiner

*Primary Examiner* — Nicholas D Lucchesi
*Assistant Examiner* — Jason Flick
(74) *Attorney, Agent, or Firm* — Westerman, Hattori, Daniels & Adrian, LLP

(57) ABSTRACT

The invention concerns a device (1) for irrigating and pressurizing a body cavity (2). Said device comprises a circuit consisting of at least one source (3), wherefrom flows a fluid under pressure, connected to a supply conduit (3) emerging in its downstream end into the cavity (2), a discharge conduit (20) for said fluid exiting from said cavity (2) and means for regulating (30) said fluid. Said regulating means (30) include first pumping means (31) capable of being temporarily engaged with the supply conduit (10), second pumping means (32) engaged with the discharge conduit (20). The two pumping means (31, 32) are operated at the same speed and in the same direction when they are engaged with their respective conduits (10, 20).

7 Claims, 3 Drawing Sheets

DEVICE FOR IRRIGATING AND PRESSURIZING A CAVITY

The subject of the present invention is a device for irrigating and pressurizing a cavity, and, in particular, a device for keeping the pressure exerted by a fluid within this cavity constant irrespective of the variations in the flow rate of this fluid.

In the field of medicine is known practice to use systems for circulating a fluid, be it liquid or gaseous, through a human or animal cavity in order to perform an endoscopic intervention therein. Typically, an intervention such as this can be used to examine or sample tissues from the cavity, for example in order to make a later diagnosis or to perform an operation by resection within this cavity in order to remove a tumor therefrom.

In order to maintain enough space to handle the instruments used during the operation, the cavity has to be pressurized in order to increase its volume slightly, at least to prevent it from contracting.

The cavity is generally pressurized by supplying a physiological saline solution and/or by blowing a gas into this cavity. Irrigating this cavity also has the purpose, during a rinsing operation, of removing the organic material originating from a resection of the tissues. Without irrigation such as this, this organic waste would soon cloud the image of the operating region provided by the endoscope. By opening into the cavity, the endoscope operating tube can also therefore be used as a supply pipe for the physiological saline solution, while the discharge pipe is able to carry the dirty saline solution to the outside where it is collected in a container.

The rate at which the saline solution circulates can be regulated by a simple valve, and more generally by a peristaltic pump. Working by compressing the discharge pipe against the pump body as shoes connected to the rotor rotate, a pump such as this can advantageously guarantee complete sterility because no mechanical part comes into contact with the pumped liquid.

The datum pressure in the supply circuit varies essentially according to the tissues of which the cavity being operated on is made. Keeping this pressure at a constant value is of key importance. This is because excess pressure could injure the cavity itself or even cause liquid to infiltrate into the patient's body. Conversely, a dropping pressure could relax the walls of the cavity, bring them into contact with the instrumentation introduced into the cavity, and cause this cavity to be accidentally punctured, with all the attendant serious consequences of this.

It is known practice for the pressure within the cavity to be adjusted using gravity by varying the head of saline solution in the supply pipe. Put differently, this amounts to varying the height at which the reservoir of physiological liquid is mounted with respect to the level of the cavity being operated on.

Better perfected, document EP 701 456 discloses a device for supplying liquid and for placing a cavity of a human or animal body under a determined pressure. To do this, a flexible pouch filled with physiological liquid is placed in a sealed container. The latter is pressurized by a pressurized air source which is connected to a pressure regulator and to a pressure gauge. The flow rate of physiological liquid, thus pressurized, is regulated downstream of the cavity by a peristaltic pump acting on the discharge pipe.

The disadvantage of this device lies in the fact that when the practitioner wishes to rinse out the cavity by significantly increasing the flow rate, this pulls a partial vacuum in the cavity as a result of the immediate increase in the rotational speed of the pump. This reduction in pressure is essentially caused by the sudden increase in the pressure drop resulting from the increased rate of flow of fluid in the upstream pipe, namely the pipe located between the liquid reservoir pouch and the cavity. Because the response time for compensating for these pressure drops is non-zero, the pressure in the cavity drops slightly before returning to its nominal value when the hydraulic system becomes stabilized at the rinsing speed. These variations in pressure result in an undesirable effect of the walls of the cavity pulsating, and this could have serious consequences should these cavities become punctured as mentioned above.

In the same field, document FR 2 766 083 discloses a device for producing a method for determining liquid losses in the irrigation circuit irrigating a human or animal cavity. To do this, the circuit comprises a supply pipe connecting a reservoir of liquid to the cavity, and a discharge pipe in which the dirty liquid is removed from the cavity to a collecting reservoir. Two peristaltic pumps positioned in this circuit circulate the liquid. One of these pumps is situated upstream on the supply pipe and the other downstream on the discharge pipe. A pressure sensor is positioned on the supply pipe, between the first pump and the cavity. The purpose of this sensor is to measure the pressure in the circuit delimited by the two pumps and to detect, via a central control unit, any significant drop in pressure due to a leak in this circuit. To do this, the method anticipates frequently stopping the two pumps in order to be able to measure the pressure difference between the start and end of the stopping of the pumps.

That device entails having, in the hydraulic circuit, a pressure sensor coupled to an additional reservoir. A sensor such as this measures the pressure of the air volume sitting on top of the surface of the liquid in this reservoir. This air also acts as a damper to prevent water hammer effects that would cause surges detrimental to the pump lying upstream. However, an air damper such as this merely attenuates the transition from one pressure value to another but does nothing either to reduce its amplitude or to eliminate any variation in pressure upon rinsing.

Furthermore, the pressure sensor of this device requires there to be a sterile microporous filter to prevent any contact between the liquid and the sensor. Now, the disadvantages caused by fitting such a filter stem from the fact that accidental contact between the liquid and the filter could corrupt the pressure measurement or even, more seriously still, completely block the pores of the filter and thus isolate the pressure sensor from any possible variation. This method also has the disadvantage of requiring the pumps to be stopped so that any drop in pressure can be detected and remedial action taken.

It is an object of the present invention to at least partially remedy the aforementioned disadvantages by suggesting a device able to regulate a fluid in a cavity while keeping the pressure constant therein in spite of temporary variations in flow rate.

To these ends, the subject of the present invention is a device according to the one described in claim 1.

The main advantages of this device lie in the fact that it is able to do away with the effect whereby the walls of the cavity pulsate as a result of variations in flow rate by guaranteeing that the pressure within this cavity will remain stable. Furthermore, it has the advantage of being of a simple, reliable and economical design while at the same time setting aside any danger to the patient of possible leakage or malfunctioning of one of the component parts of the device.

Other advantages will become apparent in the light of the description which will follow and which makes reference to a preferred embodiment taken by way of entirely nonlimiting example and illustrated by the attached figures in which.

In order to avoid any ambiguity, the terms upstream and downstream are defined as referring to the direction in which the fluid flows in the pipes of the device of the present invention.

Figure 1:
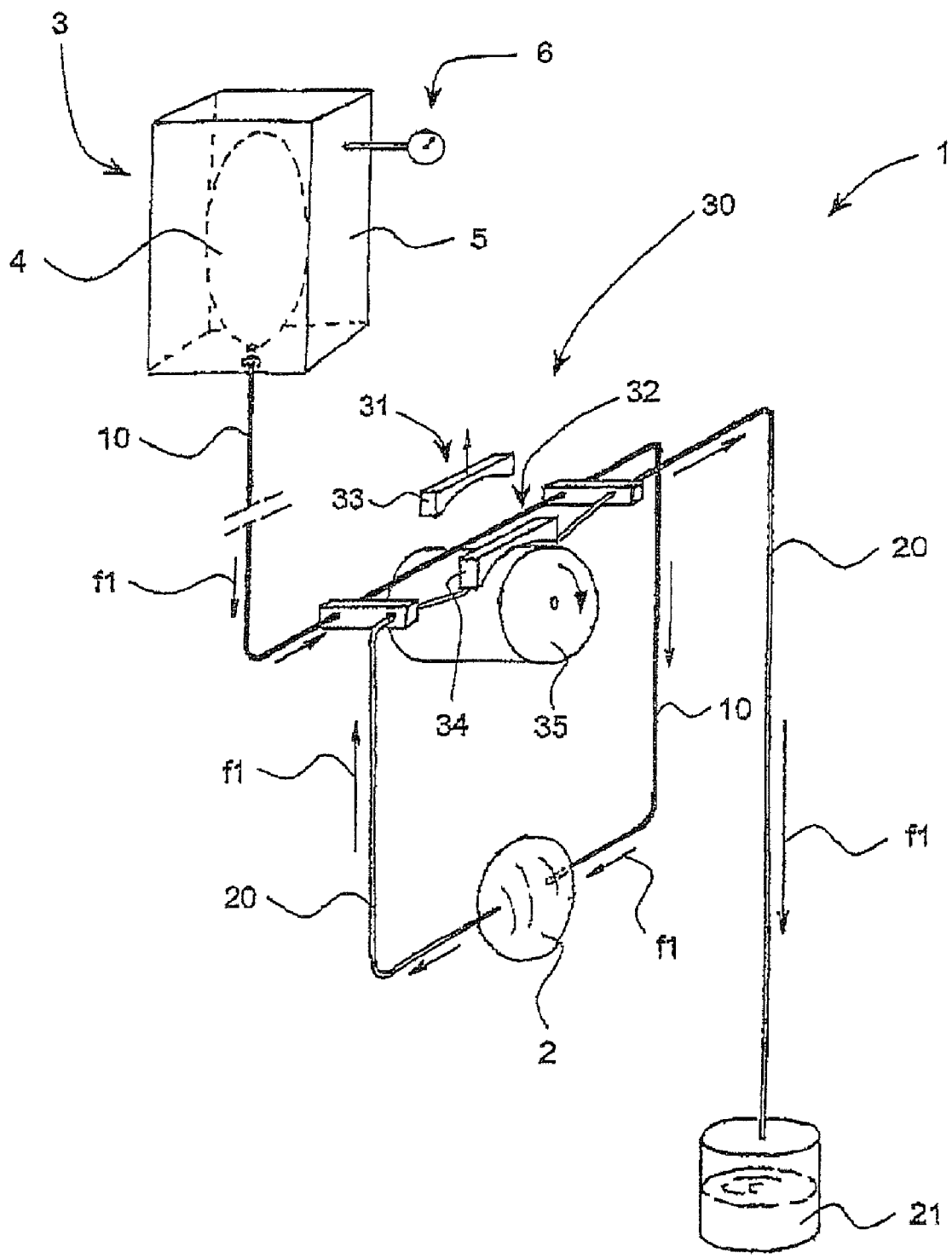
FIG. 1 is a schematic view of the device that forms the subject of the present invention, illustrated in a first state.

With reference to FIG. 1, this figure schematically illustrates the device 1 for irrigating and pressurizing an organic cavity 2, such as a cavity in a human or animal body. Starting from a source 3, a pressurized fluid flows through a circuit of pipes in the direction of the arrows f1 depicted along these pipes. These pipes are typically made of a flexible material and are generally of small diameter. As a result, the pressure drops inherent in the tubes can become relatively large when the tubes are nipped, when they form elbows or when the flow rate increases appreciably. The fluid may be pressurized in any way, for example using a flexible pouch acting as a reservoir 4 positioned in a sealed chamber 5 controlled and pressurized to a datum value using a regulator 6.

Leaving the source 3 is a supply pipe 10 opening at its downstream end into the cavity 2. Having filled and passed through this cavity, the fluid re-emerges from this cavity via a discharge pipe 20 to be finally collected in a container 21.

Regulating means 30 for regulating this fluid control its flow rate in the circuit formed by the supply pipe 10 and the discharge pipe 20. Furthermore, these regulating means are also able to keep the pressure within the cavity constant, namely to keep it at the datum value.

To do this, these regulating means comprise a first pumping means 31 which can be temporarily placed in engagement with the supply pipe 10, and a second pumping means 32 engaged with the discharge pipe 20. The expression temporarily engaged or in engagement with is to be understood as meaning that the first pumping means can be temporarily coupled or engaged with the pipe with which it is normally disassociated for most of the time.

With reference to FIG. 1, the first pumping means 31 is produced by combining a peristaltic pump rotor 35 and a first component that can move between two main positions. A component such as this is diagrammatically depicted in this figure as a first shoe 33 which can be retracted from the supply pipe 10. The first position of this shoe is the position in which it is in engagement with the supply pipe, while the second position is the one in which it is retracted from this pipe. The second pumping means 32 is preferably produced by a combination of the same peristaltic pump rotor 35 and a second moving component similar or identical to the first, such as a second shoe 34. As a preference, the second shoe 34 is intended to remain in engagement with the pipe associated with it, namely with the discharge pipe 20.

As depicted in FIG. 1, the first pumping means 31 and the second pumping means 32 together constitute a single peristaltic pump, of a particular type, that will be termed a double-pipe or double-flow peristaltic pump. Through the first shoe 33 or the second shoe 34 this pump is equipped with at least one means for neutralizing the pumping effect on at least one of the pipes 10, 20.

The way in which the device 1 of the present invention works can now be explained with the support of FIGS. 1 to 3c. When no rinsing of the cavity is demanded, the configuration of the device is the one illustrated in FIG. 1. In this first state, the first pumping means 31 is retracted from the supply pipe 10 which pipe is thus free of any stress. The pressure obtaining within the circuit, including the cavity 2, is generated by the fluid which is pressurized by the source 3 to a constant datum value. Because the source 3 is generally provided with a safety system, not depicted, no overpressurizing beyond the datum value can be generated in error, this first state corresponding to the situation in which the practitioner is carrying out an operation or making a diagnosis within the cavity 2 irrigated with a fluid such as physiological saline solution flowing at a low and constant flow rate.

When the fluid with which the cavity is filled becomes too cloudy for the intervention to continue under sensible conditions, the practitioner will operate a control to trigger the rinsing of the cavity. This operation results in a significant increase in the fluid flow rate, thus carrying any organic waste suspended therein towards the container 21, via the discharge pipe 20. The rinsing of the cavity therefore corresponds to an operation this is not only marginal but also very limited in time.

Figure 2:
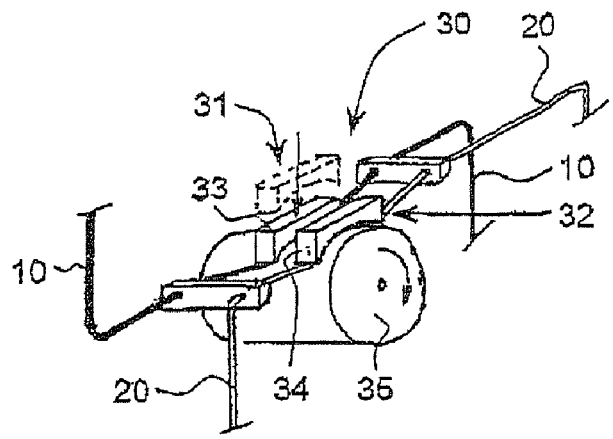
FIG. 2 depicts a portion of the device illustrated in FIG. 1, in a second state.

With each rinsing operation, the great increase in the fluid flow rate causes a significant increase in pressure drops in the circuit of the device 1. In order to prevent any reduction in the pressure inside the cavity as a result of the sudden variations in the magnitude of these pressure drops, the rinsing operation is preceded by actuation of the first pumping means 31. As illustrated in FIG. 2, this actuation in concrete terms means closing the first shoe 33 onto the supply pipe 10. This closure crushes the supply pipe and holds it against the rotor of the peristaltic pump or, more specifically, against the rollers positioned on this rotor. This second state results in a temporary closure of the section surrounding the cavity 2 and delimited, on the upstream side, by the first pumping means 31 and, on the downstream side, by the second pumping means 32. In terms of pressure, this section finds itself isolated from the remainder of the circuit and is thereby protected from any variation in pressure caused by the variations in pressure drop when the flow rates change. Once the rinsing operation has been completed, the fluid flow rate returns to its initial value after which the first pumping means 31 is deactivated, thus neutralizing the pumping effect on the supply pipe.

Figure 3A:
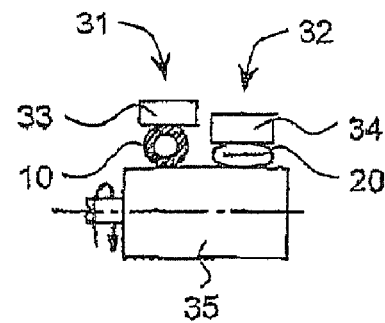
FIGS. 3a, 3b and 3c are illustrations of the various possible states, each depicted in a simplified vertical section on the axis of rotation of the pump in FIG. 2.

FIG. 3a illustrates, in a partial vertical section of FIG. 2, the first state in which only the pumping effect is applied to the discharge pipe 20 through the action of the second pumping means 32. In FIG. 2, this first state is depicted in a broken line as the retracted position of the first shoe 33.

Figure 3B:
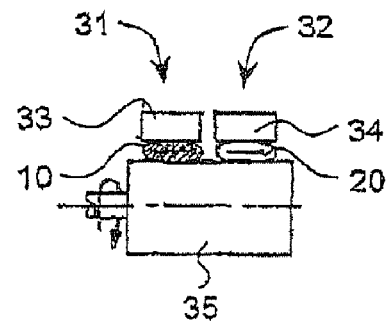

FIG. 3b illustrates, in a section similar to that of FIG. 3a, the second state in which the pumping effect is applied to both pipes 10, 20 simultaneously through the action of the corresponding two pumping means 31, 32.

Figure 3C:
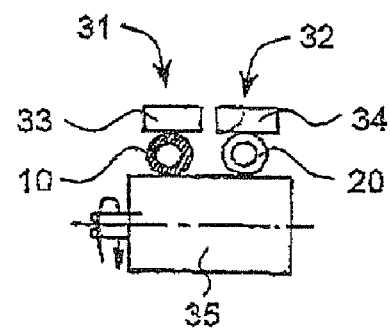

FIG. 3c represents a third situation in which irrigation of the cavity is freed by simultaneously neutralizing the pumping effect on both pipes 10 and 20. A situation such as this could arise if the second pumping means 32 were also to consist of a means disengageable from the pipe associated with it. This would result in possible uncoupling of the last two components.

Figure 4:
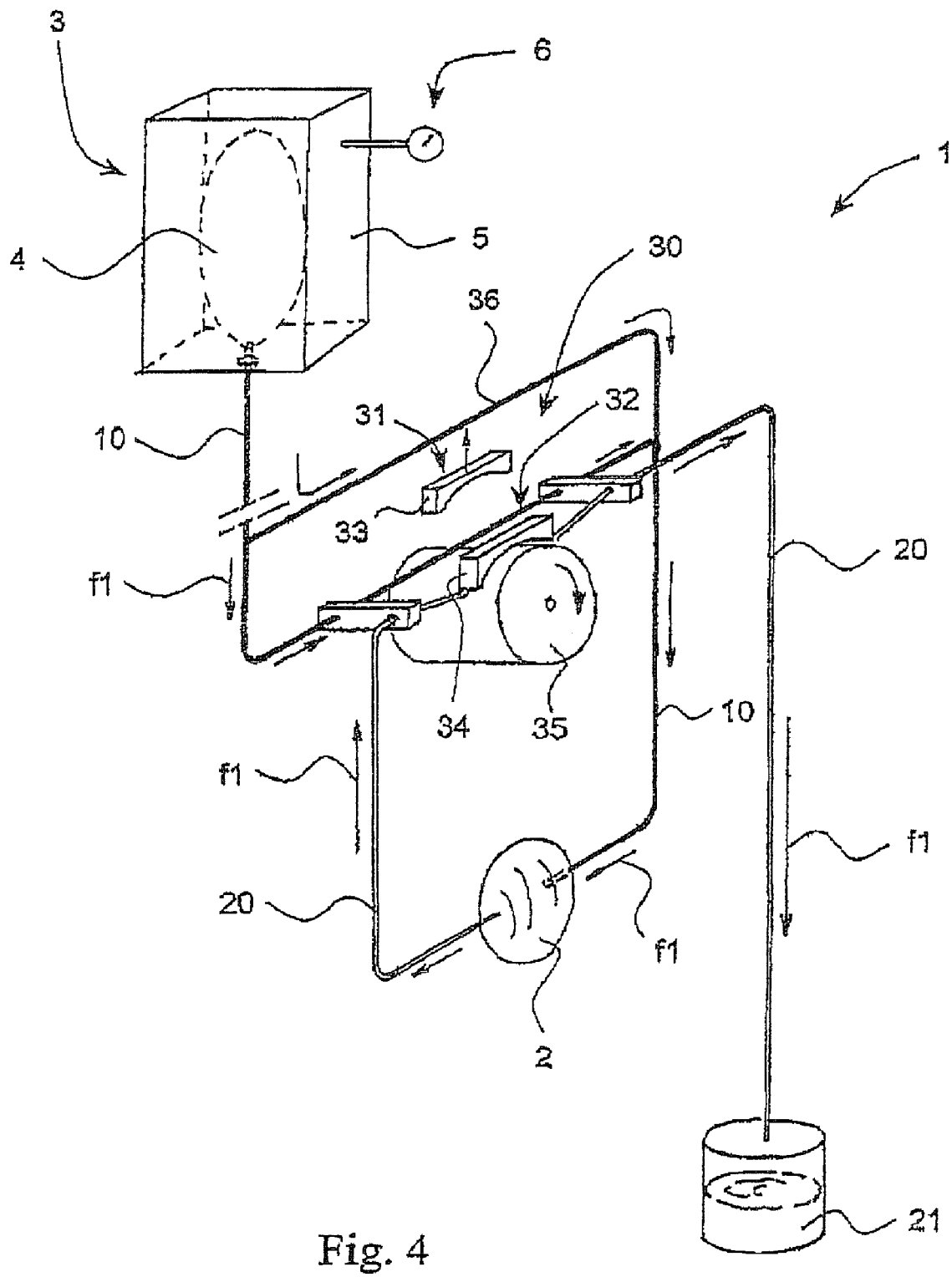
FIG. 4 illustrates a first alternative form of the device as outlined in FIG. 1.

FIG. 4 illustrates a first alternative form of the device as depicted in FIG. 1, in which the regulating means 30 also comprise a bypass pipe 36 allowing the cavity 2 to be pressurized directly, to the same pressure as the fluid. To do this, the upstream end of the bypass pipe 36 is preferably connected to the outlet of the source 3 and the downstream end of the pipe is preferably connected to the supply pipe, between the first pumping means 31 and the cavity 2. By virtue of this additional bypass pipe, the cavity can be pressurized directly, to the datum value, without passing via the first pumping means 31. Should the latter break down, the pressure within the cavity can be maintained at the datum value, thus avoiding any risk of this cavity collapsing.

Furthermore, the use of such a bypass pipe advantageously allows the two physical parameters which are the pressure and the flow rate in the circuit of the device 1 to be disassociated. Specifically, by virtue of this bypass pipe 40, it becomes possible to apply a certain datum pressure within the cavity 2 while at the same time independently choosing the flow rate for the fluid flowing through this cavity by altering the speed of the other regulating means 30, namely of the first pumping means 31 and of the second pumping means 32.

Figure 5:
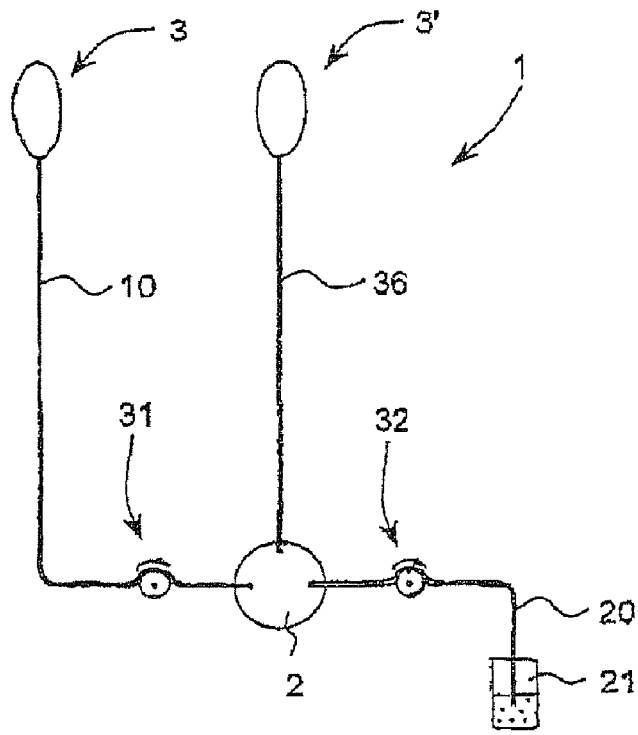
FIG. 5 depicts, in an operating block diagram, a second variant of the device that forms the subject of the present invention.

FIG. 5 depicts a functional block diagram of a second alternative form of the device that forms the subject of the present invention, in which it will be noted that the regulating means 30 consist at least of the two pumping means 31, 32 separated from one another. Thus, the first pumping means 31 consists of a peristaltic pump provided with a means 33 able to neutralize the pumping effect on the supply pipe and the second pumping means 32 consists of a second peristaltic pump, similar to the first. Although they are physically separate, the two pumps are connected to one another either mechanically or by an electrical shaft. When they are in engagement with their respective pipes, these pumps can thus be activated at the same speed, in the same direction, and preferably in phase with one another. In this second alternative form, the bypass pipe 36 leaves a pressurized second source 3' connected directly to the cavity 2. It will be understood that this diagram illustrates a more theoretical than practical variant in which the fluids from the two sources 3, 3' are, one the one hand, identical and, on the other hand, subjected to equal pressures. As a result, it will also be understood that the bypass pipe 36 could come from any point on the supply circuit 10 lying between the source 3 and the first pumping means 31. Likewise, the downstream end of this bypass pipe could be connected to any point on the supply circuit between the first pumping means 31 and the cavity 2.

With reference to FIG. 5, the arrangement of the bypass pipe 36 within the device 1 provided with two physically separate pumping means 31, 32 makes it possible to set aside any danger to the patient of possible failure of one or other of these pumping means. Specifically, should the first pumping means 31 be put out of action, the cavity 2 would still be pressurized and irrigated via the pipe 36 and operation of the second pumping means 32. Conversely, should the second pumping means 32 break down, the cavity 2 would advantageously be pressurized and irrigated by a looped circuit formed of the supply pipe 10, of the first pumping means 31 and of the bypass pipe 36.

By virtue of the double flow pump outlined in FIGS. 1 to 4, any incorrect synchronization of the two pumping means 31, 32 can advantageously be offset. Through its design, a pump such as this actually guarantees that the two pumping means will operate in phase and at the same speed when they are both in action via their respective shoes 33, 34. Advantageously also, this embodiment makes it possible to avoid any risk of an accident should the pump malfunction. Because the rotor of the peristaltic pump 35 operates the two pumping means 31, 32 simultaneously, any failure of this rotor will also put both pumping means out of action at the same time. As a result, the risk that the cavity 2 will be unintentionally emptied of its fluid through action of the second pumping means 32 alone following a failure of the first is entirely set aside. The same is true of the risk of this cavity becoming excessively inflated by action of the first pumping means 31 alone following failure of the second. Furthermore, should the double flow peristaltic pump 35 fail, the pressure within the cavity is advantageously maintained by the bypass pipe 36. As clearly illustrated in FIG. 5, any risk of fluid being drawn into the bypass pipe is also set aside by the fact that the pressures within the supply 10 and bypass 36 pipes are equal.

The invention claimed is:

1. A device for irrigating and pressurizing an organ cavity, said device comprising:
   at least one source of pressurized fluid;
   a circuit of pipes formed from the at least one source of pressurized fluid;
   a supply pipe connected to said circuit of pipes, said supply pipe opening at its downstream end into said cavity;
   a discharge pipe for said fluid re-emerging from said cavity; and
   a regulating means for regulating said fluid; said regulating means comprising a first pumping means designed to engage and disengage the supply pipe and a second pumping means designed to engage the discharge pipe,
   wherein said first pumping means includes a peristaltic pump and means for neutralizing the pumping effect on the supply pipe so that the peristaltic pump does not pump fluid in the supply pipe, said neutralizing means comprising a retractable shoe mobile between a position in engagement with the supply pipe and a position retracted from the supply pipe,
   and
   wherein said first and second pumping means are successively arranged in (i) a first position in which said first pumping means is disengaged from the supply pipe and the neutralizing means neutralizes the pumping effect on the supply pipe so that the first pumping means does not pump fluid, and said second pumping means is activated at a first speed and engages the discharge pipe so that the second pumping means pumps fluid, and (ii) a second position in which said first and second pumping means are activated at a same speed higher than the first speed and in the same direction and are both engaged with their respective pipes so that both the first and second pumping means pump fluid.

2. The device as claimed in claim 1, wherein said regulating means also comprise a bypass pipe placing the pressurized cavity at the same pressure as the said fluid.

3. The device as claimed in claim 1, wherein said peristaltic pump constitutes both the first pumping means in cooperation with the supply pipe and the second pumping means in cooperation with the discharge pipe, and said pump is equipped with the neutralizing means to neutralize the pumping effect on the supply pipe.

4. The device as claimed in claim 1, wherein the second pumping means another peristaltic pump, and said pumps of the first and second pumping means are connected to one another either mechanically or by an electric shaft.

5. The device as claimed in claim 1, wherein the pumping effect applied by the second pumping means to the discharge pipe can be neutralized by uncoupling the second pumping means from the discharge pipe.

6. The device as claimed in claim 2, wherein the second pumping means includes another peristaltic pump, and said pumps of the first and second pumping means are connected to one another either mechanically or by an electric shaft.

7. The device as claimed in claim 1, wherein said organ cavity is maintained at a constant datum pressure.

* * * * *